United States Patent [19]

Hobro et al.

[11] Patent Number: 5,714,685
[45] Date of Patent: Feb. 3, 1998

[54] METHOD AND APPARATUS FOR MEASURING THE FLOW DIFFERENTIAL IN A DIALYSIS MACHINE

[75] Inventors: Sture Hobro; Erik Linderup, both of Lund; Leif Mattisson, Sandby, all of Sweden

[73] Assignee: Gambro AB, Sweden

[21] Appl. No.: 565,730

[22] Filed: Nov. 30, 1995

[30] Foreign Application Priority Data

Dec. 7, 1994 [SE] Sweden ............................ 94.04245

[51] Int. Cl.[6] .................................................. G01F 1/68
[52] U.S. Cl. ............................... 73/204.13; 165/11.1
[58] Field of Search ........................ 73/204.11, 204.12, 73/204.13; 165/11.1

[56] References Cited

U.S. PATENT DOCUMENTS 4,530,759  7/1985  Schal .................................. 210/104
4,538,925  9/1985  Zgonik ............................. 73/204.13

FOREIGN PATENT DOCUMENTS 41 27 675 A1  2/1993  Germany.

Primary Examiner—Elizabeth L. Dougherty
Assistant Examiner—Harshad Patel
Attorney, Agent, or Firm—Lerner, David, Littenberg, Krumholz & Mentlik

[57] ABSTRACT

Methods for measuring the flow differential through a dialysis machine are disclosed in which the dialysis machine includes a heat exchanger having a primary side and a secondary side for exchanging heat therebetween. The method includes measuring the temperature differences across the primary and secondary sides of the heat exchanger and calculating the flow differential based upon these measured temperature differences. Apparatus for measuring such a flow differential is also disclosed, as are methods for calibrating that apparatus.

20 Claims, 3 Drawing Sheets

METHOD AND APPARATUS FOR MEASURING THE FLOW DIFFERENTIAL IN A DIALYSIS MACHINE

FIELD OF THE INVENTION

The present invention relates to a method and apparatus for measuring the difference between an incoming liquid flow to a dialysis machine and the outgoing liquid flow from the dialysis machine. This flow differential is related to the ultrafiltration volume which arises in a dialyser connected to the dialysis machine.

The present invention also relates to a method for calibrating such a device with the help of concentrate pumps which are normally included in a dialysis machine.

BACKGROUND OF THE INVENTION

The present invention is intended to be employed in a dialysis machine for measuring and/or monitoring the degree of ultrafiltration taking place during the dialysis procedure. A dialysis machine in which the invention can be employed is disclosed in European Pat. No. B1-0,278,100 which describes a dialysis machine corresponding essentially to the commercial dialysis machine sold under the trademark GAMBRO AK 100.

Such a dialysis machine is provided with an inlet for an incoming liquid flow, such as pure water, and one or more inlets for the addition of concentrate thereto. The liquids from these inlets are mixed to form a dialysis solution, called the dialysate, which is supplied to a dialyser.

The dialyser includes a membrane which divides the dialyser into a blood side and a dialysate side. The dialysis solution passes over the dialysate side and purifies the blood by transporting impurities such as urea from the blood through the membrane to the dialysis solution, and by transporting necessary substances such as bicarbonate from the dialysis solution to the blood. In addition, a quantity of the liquid content in the blood, i.e., blood plasma, is drawn from the blood to the dialysis solution, as the so-called ultrafiltrate.

The dialysis solution is returned to the dialysis machine and discharged as an outgoing liquid flow from the dialysis machine to a drain.

Furthermore, the dialysis machine comprises a variety of means for regulating the composition of the dialysis solution, for achieving sufficient pressure and flow conditions for the dialysis solution, as well as for regulating and transporting the blood flow on the blood side of the dialyser. Thus, the dialysis machine includes a flow measuring device for measuring the flow of dialysis solution to and from the dialyser, and for calculating the ultrafiltrate as a difference between these flows.

German Pat. No. A1-4,127,675 discloses a method and apparatus for monitoring the fluid flow in a conduit. A heat impulse is supplied to the fluid and the increase of temperature due to the supplied heat energy is used as a measurement of the mass flow through the conduit. The principle is called a thermal flow meter.

U.S. Pat. No. 4,530,759 discloses a method and apparatus for measuring the ultrafiltrate in a dialysis machine using a balancing device. The balancing device induces an error in the ultrafiltrate measurement due to different temperatures in the two balancing chambers, resulting in a small change of density. This error is compensated for by measuring the temperature difference and applying a correction factor thereto.

In a medical dialysis apparatus, it is customary to use a second independent measuring device for purposes of safety while monitoring significant properties and operating parameters of the dialysis machine.

The principal object of the present invention is to provide a device which monitors the ultrafiltrate totally independently of the normal operation of the dialysis machine.

SUMMARY OF THE INVENTION

In accordance with the present invention, these and other objects have now been accomplished by the invention of a method for measuring the flow rate differential through a dialysis machine including ultrafiltration means for effecting ultrafiltration and a heat exchanger including a primary side and a secondary side for exchanging heat between the flow of an inlet fluid having an inlet flow rate through the primary side of the heat exchanger into the dialysis machine and the flow of an outlet fluid having an outlet flow rate outlet flow through the secondary side of the heat exchanger from the dialysis machine comprising measuring the temperature differences across the primary and secondary sides of the heat exchanger and calculating the flow rate differential based upon the measured temperature differences.

In accordance with a preferred embodiment of the method of the present invention, the method includes determining the total flow rate of the inlet flow or the outlet flow, and calculating of the flow differential is based upon the equation $$\Delta Q = Q \times (\Delta T_1 - \Delta T_2)/\Delta T_2$$

wherein $\Delta Q$ represents the flow differential, Q represents total flow rate of the inlet flow or the outlet flow, $\Delta T_1$ represents the temperature difference across one of the primary and secondary sides of the heat exchanger and $\Delta T_2$ represents the temperature difference across the other of the primary and secondary sides of the heat exchanger. In a preferred embodiment, determining of the total volume is carried out by means of a thermal flow meter.

In accordance with another embodiment of the method of the present invention, the method includes determining heat capacities for the inlet fluid and the outlet fluid, and calculating of the flow rate differential includes compensating for differences in these heat capacities.

In accordance with another embodiment of the method of the present invention, the method includes determining the heat energy losses in the heat exchanger and the dialysis machine, and calculating of the flow rate differential includes compensating for the heat energy losses.

In accordance with another embodiment of the method of the present invention, determining of the total flow rate is carried out utilizing a nominal value of the inlet flow rate or the outlet flow rate. Preferably, this nominal value comprises a desired flow value for a predetermined user.

In accordance with another embodiment of the method of the present invention, the dialysis machine includes a heater, and determining of the total flow rate includes measuring the temperature differences across the heater, and measuring the power supplied to the heater, the calculating of the total flow rate being based upon the equation $$Q = k \times P/\Delta T$$

wherein k represents a constant, P represents the power supplied to the heater, and $\Delta T$ represents the temperature differences across the heater. In a preferred embodiment, the measuring of the power supplied to the heater is corrected by calculating losses to the environment.

In accordance with another embodiment of the present invention, an apparatus is provided for measuring the flow rate differential through a dialysis machine comprising a flow inlet for a flow of an inlet fluid having an inlet flow rate to the dialysis machine, a flow outlet for an outlet fluid having an outlet flow rate from the dialysis machine, ultrafiltration means for effecting the flow of an ultrafiltration fluid in the dialysis machine, a heat exchanger including a primary side and a secondary side for exchanging heat between the flow in the flow inlet and the flow in the flow outlet, temperature sensor means for measuring the temperature differences across the primary and secondary sides of the heat exchanger, and calculating means for calculating the flow differential based upon the measured temperature differences.

In accordance with one embodiment of the apparatus of the present invention, the calculating means employs the equation $$\Delta Q = Q \times (\Delta T_1 - \Delta T_2)/\Delta T_2$$

in which $\Delta Q$ represents the flow differential, Q represents the total flow rate of the inlet flow or the outlet flow, $\Delta T_1$ represents the temperature difference across one of the primary and secondary sides of the heat exchanger, and $\Delta T_2$ represents the temperature difference across the other of the primary and secondary sides of the heat exchanger.

In accordance with one embodiment of the apparatus of the present invention, the apparatus includes concentrate inlet means for the addition of a concentrate at a concentrate flow rate to the flow rate if the inlet fluid the In a preferred embodiment, the calculating means includes heat capacity compensation means for compensating for differences in the heat capacity of the inlet fluid and the outlet fluid, the heat capacity compensation means employing the equation $$\Delta Q_c/Q_1 = (1 - C_1/C_2) \times \Delta T_1/\Delta T_2$$

in which $\Delta Q_c$ represents a flow rate correction factor based upon the differences in the heat capacities, $Q_1$ represents the total flow rate, $C_1$ represents the heat capacity of the inlet fluid and $C_2$ represents the heat capacity of the outlet fluid.

In accordance with another embodiment of the apparatus of the present invention, the calculating means includes heat energy loss means for compensating for losses of heat energy in the heat exchanger and the dialysis machine, the heat energy loss means employing the equation $$\Delta Q_p/Q_1 = (1 - P_2/P_1) \times \Delta T_1/\Delta T_2$$

in which $\Delta Q_p$ represents a flow rate correction factor for the losses of heat energy, $Q_1$ represents the total flow rate, $P_2$ represents the heat energy loss in the flow of the inlet fluid and $P_1$ represents the heat energy loss in the flow of the outlet fluid.

In accordance with another embodiment of the apparatus of the present invention, the calculating means utilizes a nominal value of the flow of liquid in the inlet or the flow of liquid in the outlet. Preferably, the nominal value comprises a desired flow value for a predetermined user.

In accordance with another embodiment of the apparatus of the present invention, the apparatus includes a heater, and the calculating means includes temperature measuring means for measuring the temperature difference across the heater, and power supply means for measuring the power supplied to the heater, wherein the calculating means is based upon the equation $$Q = k \times P/\Delta T$$

in which k represents a constant, P represents the power supplied to the heater, and $\Delta T$ represents the temperature difference across the heater. In a preferred embodiment, the means for measuring the power supplied to the heater is corrected by calculation of the losses to the environment.

In accordance with another embodiment of the apparatus of the present invention, the apparatus includes a heater, and the heat exchanger and the heater include insulation jacket means.

In accordance with another embodiment of the present invention, a method is provided for calibrating apparatus for measuring the flow differential through a dialysis machine including ultrafiltration means for effecting ultrafiltration, a heat exchanger including a primary side and a secondary side for exchanging heat between the inlet flow through the primary side of the heat exchanger into the dialysis machine and the outlet flow through the secondary side of the heat exchanger from the dialysis machine, and concentrate supply means for supplying a concentrate to the inlet flow, the method comprising discontinuing the ultrafiltration by disconnecting the ultrafiltration means from the dialysis machine while continuing to operate the dialysis machine, varying the amount of concentrate supplied to the inlet means by the concentrate supply means, and measuring the flow differential based upon variation of the amount of concentrate.

According to the present invention, the use of a thermal flowmeter for measuring the ultrafiltration is proposed.

A thermal flowmeter uses the following equation:

$$P = Q \times C \times \Delta T \quad (1)$$

in which P is the power which is supplied to the liquid and which brings about a change in the temperature of $\Delta T$ during a mass flow Q, in which C is the heat capacity of the liquid.

It is also noted that many dialysis machines already include, either initially or as a later added option, a heat exchanger which recovers a quantity of the heat content in the outgoing liquid flow from the dialysis machine and transfers this heat content to the incoming liquid flow to the dialysis machine. In this manner, the heating requirement within the dialysis machine is reduced, which is an advantage particularly when the available power supply is limited. The heat exchanger can be built into the machine, or it can be arranged as an accessory outside of the machine itself.

The transfer of such heat energy occurs in the heat exchanger from the secondary side to the primary side. The transferred heat energy can be expressed as a loss of heat energy when the liquid passes through the secondary side of the heat exchanger and/or as an addition of heat energy when the liquid passes through the primary side of the heat exchanger. The flow differential between the secondary side and primary side of the heat exchanger can be expressed as a function of the temperature differences across the primary side and the secondary side, as well as the total flow through the heat exchanger.

In a preferred embodiment of the present invention, the total flow through the primary side of the heat exchanger is measured with a second thermal flowmeter within the dialysis machine. The dialysis machine comprises a heating device for heating the incoming liquid flow to approximately body temperature, for example 38° C. By measuring the temperature increase across the heating device, as well as the supplied electrical power, the flow through the heating device can be calculated according to equation (1) above.

As mentioned above, the dialysis machine also includes inlets for concentrate. These inlets contribute to the flow differential mentioned above. In order to obtain the ultrafiltrate, the incoming concentrate flows must be subtracted from the calculated flow differential. However, additions of the concentrate occur by means of dosage pumps with known and constant displacement, for example ceramic pumps. Accordingly, the concentrate flows are known, so that the ultrafiltrate can therefore be calculated. Compensation can also be made for power losses which affect the thermal processes, as well as for changes in the heat capacity, and for the density of the fluids involved.

According to the present invention, one of the concentrate pumps can be used to calibrate the ultrafiltration measuring device. Thus, the dialyser is shunted so that no ultrafiltration takes place and the concentrate pumps are set to predetermined "ordinary" values. Then, one of the concentrate pumps is set to an increased flow and the measuring device according to this invention is calibrated in principle to correspond to the increased value of that concentrate pump.

BRIEF DESCRIPTION OF THE DRAWINGS

Further objects, advantages and features of the present invention will be apparent from the following detailed description of preferred embodiments of the invention, with reference to the attached drawings, in which.

DETAILED DESCRIPTION

Figure 1:
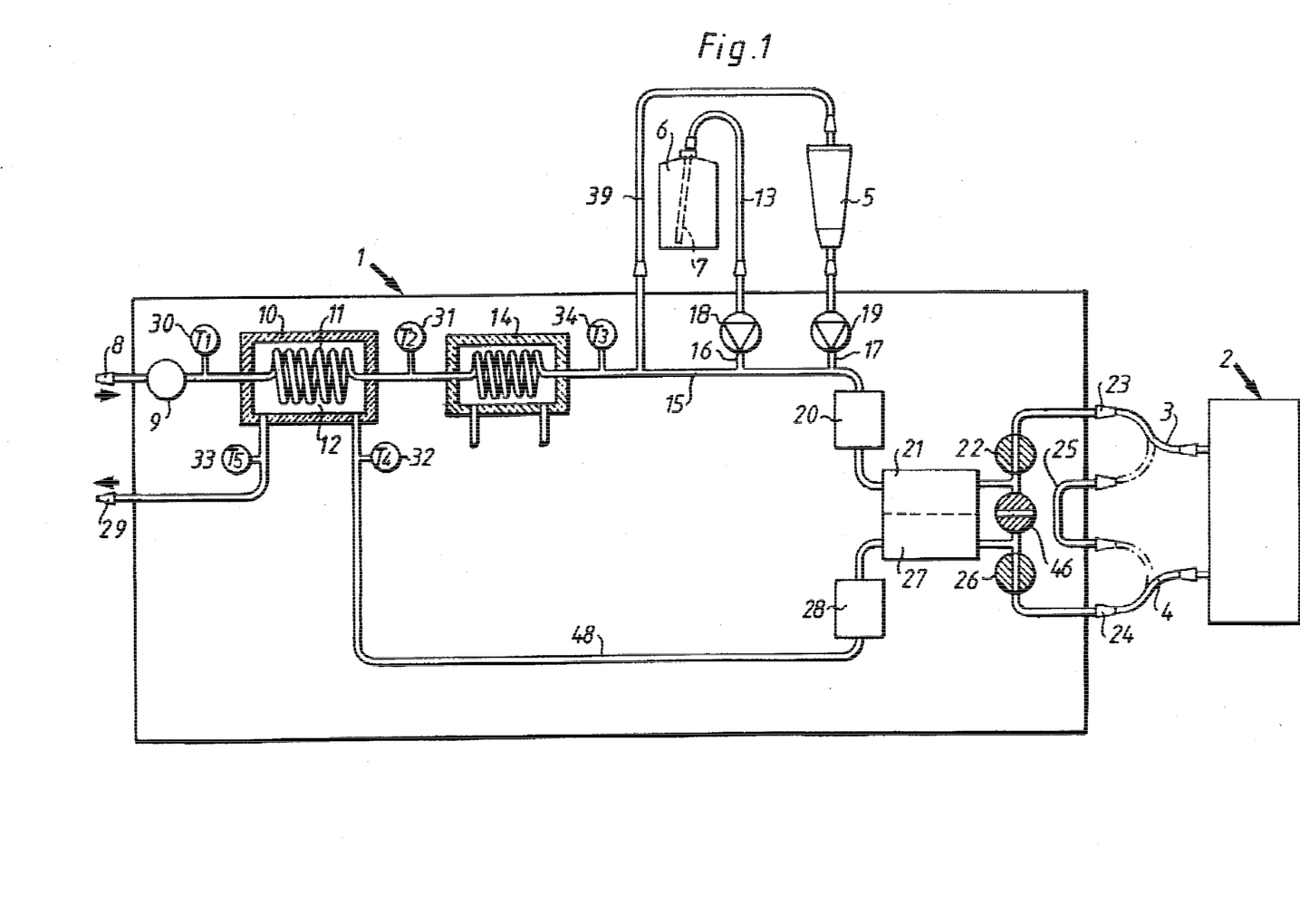
FIG. 1 is a schematic view of a measuring device according to the present invention connected to a dialysis machine.

Referring to the drawings, in which like reference numerals refer to like elements thereof, a dialysis machine is shown in FIG. 1 to which the present invention can be applied.

The dialysis machine 1 comprises an inlet 8 for pure water. By means of a valve 9, inlet 8 leads to the primary side 11 of a heat exchanger 10. The valve 9 can be a shut-off valve and/or a pressure regulating valve.

From the primary side 11, water is fed to a heating device 14 where the incoming water is heated to approximately body temperature, for example about 38° C. The water passes from the heating device 14 through a conduit 15 provided with two inlets, 16 and 17, for concentrate.

The first inlet 16 is associated with a container 6 which contains A-concentrate (acid concentrate). The concentrate in the container 6 is drawn up by a pick-up tube 7 and passes through a tube 13 to a concentrate pump 18. The concentrate pump 18 is, for example, a ceramic-type pump and consists of a very accurate dosage pump. The volume of concentrate which is introduced through inlet 16 is thus very accurately determined by the number of revolutions of the dosage pump 18.

A second concentrate, namely a B-concentrate (bicarbonate concentrate), is introduced through the second inlet 17 by means of a second concentrate pump 19. Water is drawn through a branch conduit from conduit 15 slightly downstream of the heating device 14, and is introduced into the upper part of a cartridge 5 containing the bicarbonate in powder form. The water passes through the powder and forms a solution of bicarbonate which is substantially saturated. By means of concentrate pump 19, the desired quantity of B-concentrate is introduced through inlet 17.

Conduit 15 also includes various devices which are necessary in a dialysis apparatus, such as conductivity cells for measuring and controlling the dosage pumps 18 and 19. In addition, a degassing device, a pump device, a pH-measurer and other such devices are provided. These devices are symbolized by the box 20, but can be located at different points along the conduit 15. Downstream of the device 10, the thus prepared dialysate is supplied to a first flow measuring cell 21, and then through a valve 22 to a dialysate outlet 23.

A dialyser is shown schematically by reference numeral 2 and is provided with a tube 3 for connection to the dialysate outlet 23, as well as a tube 4 for connection to a dialysate inlet 24. As indicated by dashed lines in FIG. 1, tubes 3 and 4 can be connected to a shunt conduit 25, for example during the start-up phase of the machine, as well as during disinfection, etc.

Dialysis of the blood occurs in the dialyser, which means that ions pass through the membrane of the dialyser from the dialysate to the blood and vice versa. In addition, a fixed quantity of blood plasma is drawn out in the form of an ultrafiltrate.

The dialysis solution flows from the dialysate inlet 24 through a valve 26 to a second flow measuring cell 27, then through a number of devices which are symbolized by box 28 to the secondary side 12 of the heat exchanger 10, and then to an outlet 29 which is normally connected to a drain. Box 28 contains, for example, a blood leakage detector, a pump device, pressure and temperature measurers, etc., which are positioned at various points along the conduit 48 from the dialysate inlet 24 to the outlet 29.

As is apparent from FIG. 1, an inlet 8 for water is provided which, in this description, is termed 20 the incoming flow. In addition, there is an outlet 29 for the consumed dialysate which, in this description, is denoted as the outgoing flow. The incoming and outgoing flows lead to and come from the heat exchanger 10.

In the dialysis machine, certain additions are made to the incoming flow. At the inlet 16, concentrate is introduced from an external container 6, and is thus added to the incoming flow.

At the inlet 17, concentrate is added from a powder cartridge 5. Removal of a flow through a branch conduit from the conduit 15 occurs simultaneously. The net addition through inlet 17 is thus substantially zero, since the same quantity is removed from the conduit 15 through the branch conduit as is added to the conduit 15 through the inlet 17. When the powder dissolves in the cartridge 5, substantially no, or a very small, volume change takes place, though the density and the heat capacity are altered.

An addition of fluid volume to the incoming flow occurs in the dialyser 2 in the form of the ultrafiltrate. It is this ultrafiltrate which is to be monitored according to the present invention. The ultrafiltrate is measured in the dialysis machine as a difference between the flow through the second measuring cell 27 and the flow through the first measuring cell 21.

It will thus be apparent that the difference between the incoming flow through the inlet 8 and the outgoing flow through the outlet 29 consists of the addition of concentrate via the inlet 16 from the container 6, as well as the ultrafiltrate.

In certain machines, the conduit 39 and the cartridge 5 are replaced by a container containing concentrate. In that case, a net addition of a liquid volume to the incoming flow through the inlet 17 will, of course, occur. Other machines may have only one inlet corresponding to the inlet 16. Machines are also known which use several cartridges 5 with powder concentrate and only small quantities of liquid concentrate.

An increase in the temperature of the incoming flow takes place on the primary side 11 of the heat exchanger 10. This increase in temperature is measured by two temperature sensors, 30 and 31, which measure the temperature $T_1$ upstream of the heat exchanger and the temperature $T_2$ downstream of the heat exchanger, respectively. On the secondary side of the heat exchanger there are two temperature sensors, 32 and 33, which measure the incoming temperature $T_4$ to the secondary side of the heat exchanger and the outgoing temperature $T_5$. In addition, a further temperature sensor 34 is positioned downstream of the heating device 14 to measure the outgoing temperature $T_3$ from the heating device.

With the help of the temperature sensors 34 and 31, as well as by measuring the energy addition to the heating device 14, the total incoming flow can be calculated. The calculation occurs with the above equation (1). In order to obtain an accurate value of the flow, it may be necessary that the heating device 14 be heat insulated relative to the surroundings, so that the supplied electrical power is really transferred to the liquid. Alternatively, or in addition, the supplied power can be compensated for by possible emissions to the surroundings.

A transfer of heat energy takes place in the heat exchanger from the secondary side of the heat exchanger to its primary side. If the heat exchanger is well insulated, these quantities of heat energy are equally large. If the primary side is denoted by suffix 1 and the secondary side is denoted by suffix 2, the following equation is obtained according to the above equation (1):

$$Q_1 \times C_1 \times \Delta T_1 = Q_2 \times C_2 \times \Delta T_2 \qquad (2)$$

If it is assumed that $C_1=C_2$ and $Q_2=Q_1+\Delta Q_1$, the following equation is obtained:

$$\Delta Q_1/Q_1=(\Delta T_1-\Delta T_2)/\Delta T_2 \qquad (3)$$

$\Delta Q_1$ thus corresponds to the additions which take place within the dialysis machine between the primary side of the heat exchanger and its secondary side. These additions occur in FIG. 1 through the inlet 16, $Q_A$, as well as the ultrafiltration, $Q_u$, in the dialyser 2. The quantity which passes through the inlet 16 is known, since the dosage pump 18 is very accurate. Thus, the quantity of ultrafiltration can be determined.

In equation (3), it is assumed that the heat capacity for the incoming flow, normally pure water, through the inlet 8 is the same as the heat capacity for the outgoing flow through the outlet 29. This is not totally correct, since salts have been added via inlets 16 and 17, which change the density of the liquid, as well as to a certain extent its specific heat capacity. The additional flow through the dialyser 2 also changes these conditions somewhat.

An analysis of equation (2) shows, however, that a small constant change of the heat capacity gives only a substantially constant addition to the calculated flow differential $\Delta Q_1$ calculated according to equation (3) with a correction factor $\Delta Q_c$ according to equation (4):

$$\Delta Q_c/Q_1=(1-C_1/C_2)\times \Delta T_1/\Delta T_2 \qquad (4)$$

If $\Delta T_1/\Delta T_2$ is constant, which is the case during measurement of a small flow differential $\Delta Q_1$, the addition will be approximately constant.

The same applies if it is assumed that a fixed portion of the heat energy on the secondary side is emitted to the surroundings. The correction factor $\Delta Q_p$ is thus determined by the following equation (5):

$$\Delta Q_p/Q_1=(1-P_2/P_1)\times \Delta T_1/\Delta T_2 \qquad (5)$$

Accordingly, the ultrafiltration $\Delta Q_u$ is obtained according to the following equation (6):

$$\Delta Q_u=\Delta Q_1-\Delta Q_A-\Delta Q_c-\Delta Q_p \qquad (6)$$

The size of the correction factors can be measured during start up of the dialysis machine with those parameters which are necessary for the dialysis treatment in question.

It is to be noted that the heat capacity for the ingoing and outgoing liquid flow is also dependent on its oxygen content and the content of other gases, and thus account can also be taken of these factors.

It is apparent from the above equations that the calculation is based on measurement of the differences between two or four temperatures. It is desirable to perform the necessary calculations in a computer. If the measured temperatures are digitalized and the calculation of the difference is performed by the computer, digitalization errors will easily affect the result. In such case, A/D converters with very high resolution must be used, which in principle integrate the measured temperature value over a relatively long period.

Figure 2:
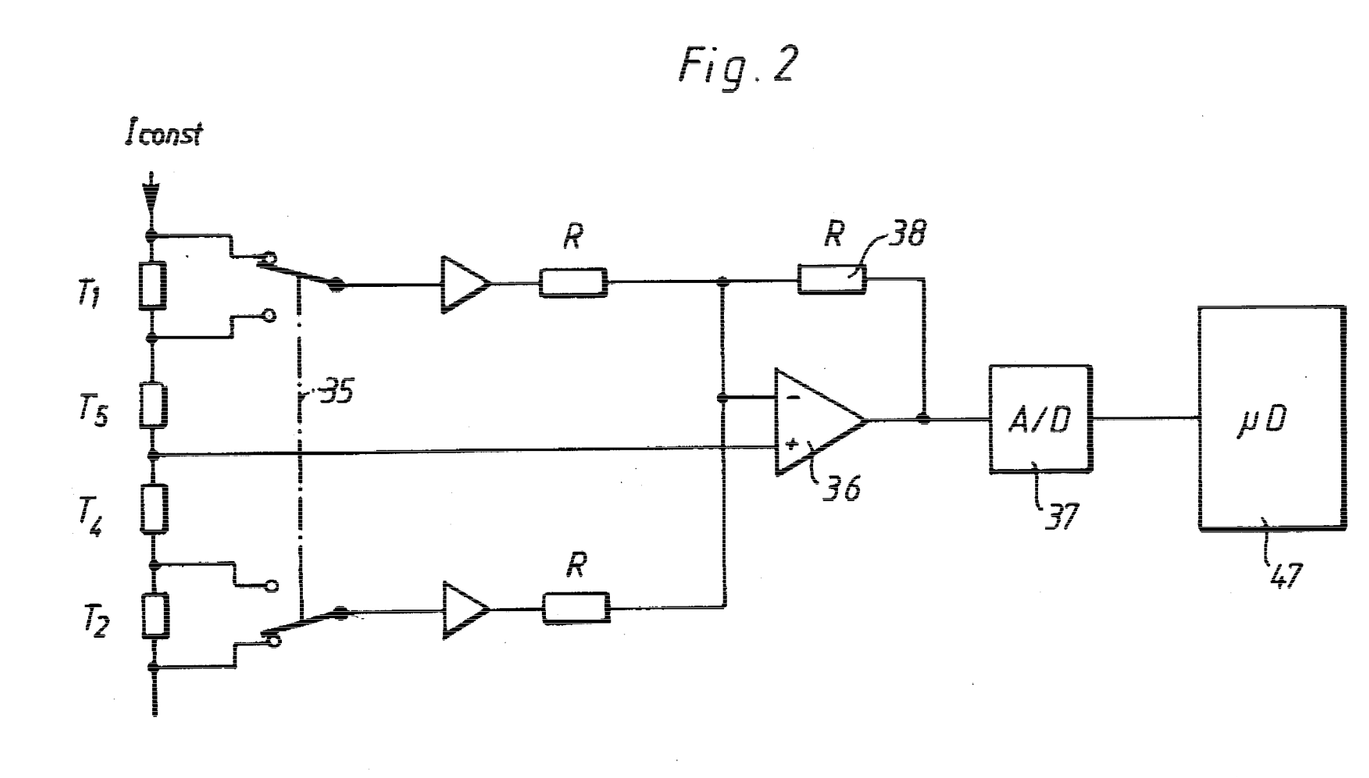
FIG. 2 is a schematic diagram representing how the measuring device of the present invention can be arranged in order to achieve reliable measuring values.

Since it is $\Delta T_1-\Delta T_2$ and $\Delta T_2$ which are of interest, according to a preferred embodiment of the present invention, it is proposed to connect the temperature sensors in the manner shown in FIG. 2. The temperature sensors which are employed consist of heat sensitive resistors, i.e., thermistors, in which the resistance is substantially proportional to the temperature. If these thermistors are connected in series in the manner indicated in FIG. 2, $\Delta T_2$ and $\Delta T_1-\Delta T_2$, respectively, can be measured by adjustment of the switch 35. The thermistors, $T_2$, $T_4$, $T_3$ and $T_1$ are connected in series and a common constant current $I_{const}$ passes through the thermistors. The current is generated by a constant current generator (not shown).

The Mid-point between the thermistors $T_5$ and $T_4$ is connected to the positive input of an OP amplifier 36. The voltage which arises before the thermistor $T_1$ and after the thermistor $T_2$, respectively, is fed through the switch 35 to the negative input of the OP amplifier 36. Thus, a voltage is obtained from the output of the OP amplifier 36 which corresponds to $(-T_1-T_5+T_4+T_2)=\Delta T_1-\Delta T_2$. By switching the switch 35 to the second position, the voltage from the thermistor $T_5$ and thermistor $T_4$, respectively, is fed to the OP amplifier 36 and the output thereof provides a voltage corresponding to $(-T_1+T_4)=-T_2$. The two voltages thus attained are fed to an AD converter 37 and further to a calculating computer 47.

In the position shown in FIG. 2, $\Delta T_1-\Delta T_2$ is measured, and has a very much lower value than $\Delta T_2$, which is measured in the second position of switch 35. The switch 35 can be complimented by a further section which alters the value of the resistance 38 which determines the amplification of the OP amplifier 36 so that the amplification increases by a suitable factor, for example by a factor 10. In this manner an AD converter 37 with lower resolution can be used.

By providing the computer 47 with measurement values of $\Delta T_2$, and the difference $\Delta T_1-\Delta T_2$, the computer can calculate $\Delta T_1$ and thus also the ratio $\Delta T_1/\Delta T_2$. This can be used to calculate $\Delta Q_c$ and/or $\Delta Q_p$ according to equations (4) and (5) above. All of this assumes that the ratios $C_1/C_2$ and/or $P_1/P_2$ are known. The ratio $C_1/C_2$ is a function of the temperature of the incoming and outgoing liquid, their salt concentrations and densities, dissolved or dispersed gases in the liquids, as well as other factors. The calculating computer 47 can calculate this ratio, though it sometimes requires further information, such as the temperature of the incoming water $T_1$ or $T_2$.

If $T_2$ is measured, this can also be used to calculate $Q_1$, i.e., the incoming flow, by means of using the above equation (1) and the heating device 14. $T_3$ is regulated by the dialysis machine to a predetermined temperature, for example, 38° C. Thus, if $T_2$ is known, then so too is the difference $T_3-T_2$ across the heating device. By measuring the addition of power to this device, i.e., the current and voltage, the flow $Q_1$ can be calculated.

Since temperature differences are of interest, it can be practical to employ a thermal element, or a so-called thermocouple, where the voltage is attained across the thermocouple which is proportional to the temperature difference between two points or joints. The thermal element uses the property that a potential difference arises at the junction between two conductors or different material, for example, copper and iron. The potential difference is temperature-dependent. By using two junction locations which have different temperatures, a voltage arises across the thermocouple. In this manner, the voltage which arises can be digitalized and forms a measurement of $\Delta T_1$ and $\Delta T_2$, respectively.

Figure 3:
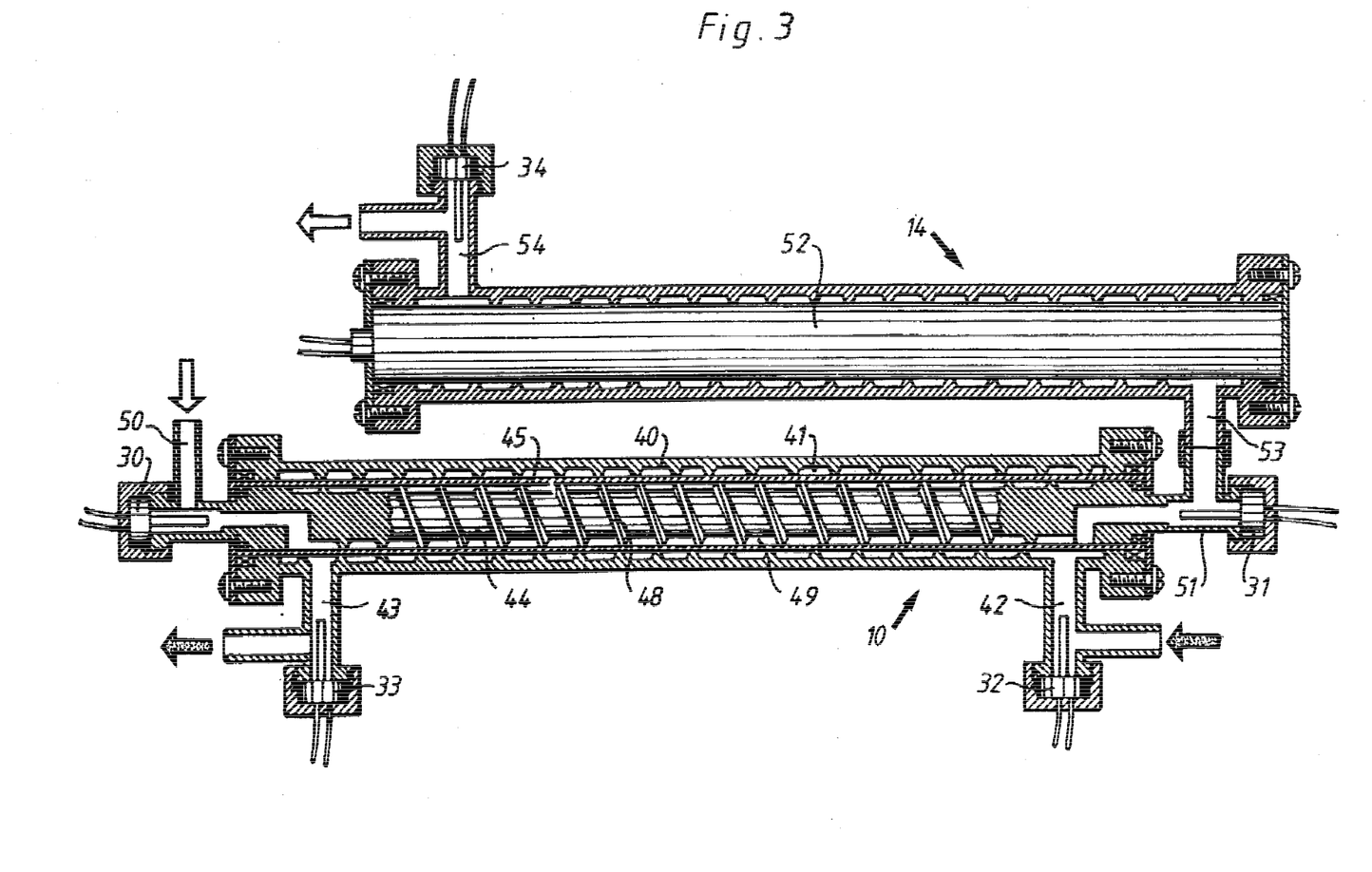
FIG. 3 is a side, elevational, cross-sectional view of a heat exchanger and heating device which can be used in accordance with the present invention.

According to the present invention, other methods can also be used for measuring the total incoming flow $Q_1$, such as by measuring the pressure difference across a throttling device, or by using some other flow meter. It is also possible to use an estimated or nominal value, for example, a value inputted by the user. A cross-section of a heat exchanger 10 and a heating device 14 is shown in FIG. 3 which may be utilized according to the present invention. The heat exchanger 10 consists of an outer sleeve 40 in the form of a tube. The inner surface of the tube is provided with a spiral-shaped groove 41 which runs from an inlet 42 to an outlet 43. The inlet 42 and the outlet 43 are provided with temperature sensors, 32 and 33, respectively. The spiral-shaped groove 41 is delimited inwardly by a metal cylinder 45. The thus-described components together form the secondary side of the heat exchanger.

Within the metal cylinder 45, an inner cylinder 44 is located, which is provided with threads 48. The threads 48 seal against the metal cylinder 45 and form a screw-shaped groove 49 which forms the primary side of the heat exchanger. An inlet 50 is provided with a temperature sensor 30, and an outlet 51 is provided with the temperature sensor 31.

The heating device 14 consists of the same outer sleeve 40 as the heat exchanger, though the metal cylinder 45 is replaced by a heating cartridge 52. The heating device 14 is located close to the heat exchanger 10 so that the temperature sensor 31 can be regarded as measuring the input temperature to the heating device 14. The heating device thus has an inlet 53 and an outlet 54, whereby the outlet is provided with the temperature sensor 34.

The temperature sensors are of the type Pt 100 (thermistor) and consist principally of a thin metal tube containing a heat sensitive resistor, as well as a connection head through which connection conduits pass.

In order to obtain an estimation as to how large the power losses to the surroundings are, a temperature sensor (not shown) can be used which measures the surrounding temperature within the dialysis machine and/or outside of same.

With the help thereof, the calculating computer can estimate the power losses in the heat exchanger 10, the heating device 14, and the dialysis machine in general.

It may also be possible to reduce the power loss to the surroundings by heating the heat exchanger's surroundings to a temperature approaching the average value of $T_4$ and $T_5$. Thus, the heat exchanger 10 can possibly attain a heat energy surplus from the surroundings. In certain applications, it is suitable to insulate the heat exchanger 10 and/or the heating device 14 by surrounding them with heat-insulating material of suitable thickness.

In order to obtain the necessary accuracy for measurement of the flow differential through the heat exchanger and according to this invention, it is necessary that sufficient temperature differences be attained across the heat exchanger, for example at least 5° C. between the inlet and the outlet on the primary side. This is normally not difficult to obtain since the temperature of the incoming flow is normally less than around 20° C. In warmer countries, where the temperature can approach 30° C., it can be problematic to achieve sufficient accuracy in measuring the flow differential. The calculating computer 47 can thus be arranged to warn the user that measurement of the ultrafiltrate is taking place with reduced accuracy.

To obtain a practically useful measuring device for the flow differential of the ultrafiltrate, it can be suitable to calibrate the measuring device each time that it is used. This is possible to effect with the components which are normally present in the dialysis machine, and in the dialysis machine according to FIG. 1 with the help of the dosage pump 18.

During the start up of a dialysis machine, the dialyser 2 is "primed" by allowing normal dialysis solution to pass on the dialysis side of the dialyser 2, while sterile salt solution passes on the blood side. In doing so, the dialysis machine is operated so that it produces dialysis solution with normal concentration through the dosage pumps, 18 and 19.

According to the present invention, calibration is attained in the following manner. The dialysis machine is started in a normal manner and the dialyser is "primed," whereby the dialysis machine attains normal operating temperatures. Thereafter, valves 22 and 26 are switched so that the dialyser 2 is disconnected and a shunt valve 46 is connected in and shunts the dialysate flow from the measuring cell 21 to the measuring cell 27. This connection is used to calibrate the measuring cells 21 and 27 to the same flow.

By measuring the temperature differences in the heat exchanger 10 in this position, a fixed flow differential is obtained with regard to the inflow through inlet 16, $\Delta Q_A$, the difference in the heat capacity between the incoming flow and the outgoing flow, $\Delta Q_c$, as well as power losses in the heat exchanger, $\Delta Q_p$, since the ultrafiltration in this connection is zero. The three correction factors in the equation (6) can thus be determined.

Thereafter the speed of the dosage pump 18 is increased by a predetermined value, for example an increase of 10 ml/min. from, for example, about 15 ml/min. to about 25 ml/min. This provides a simulation of an ultrafiltration of 10 ml/min. and the new value of $\Delta Q_1$ in the heat exchanger is read off by the calculating computer. In this manner, a calibration factor is attained which can be used for calculating the ultrafiltration in the subsequent measurings.

By the addition of an extra quantity of concentrate through inlet 16, an increase in the heat capacity $C_2$ and the density of the outgoing flow is obtained. This change is small, however, and can be ignored or compensated for by the calculating computer.

The correction factor which arises during this calibration can depend on possible original measuring errors in the measuring value of the total incoming flow $Q_1$, or by diverse losses of other types. The calibration can also be used to obtain a nominal value of the incoming flow $Q_1$ which is later used in subsequent calculations, i.e., measuring of $Q_1$ is not required.

In the above discussion, measurement of the incoming flow $Q_1$ has been given which is normally preferred when the conditions are favorable for measurement of precisely that incoming flow. Nothing prevents the outgoing flow $Q_2$ to be measured (or estimated), if it should be preferred in a particular case. The different equations will, in principal, be the same as those given above, but with altered suffixes. The use of the outgoing flow $Q_2$ as a basis for the calculations is obviously equivalent.

The invention has been described above with the aid of preferred embodiments described with reference to the drawings. The various properties and features can be combined in other ways than those given in the drawings, which will be obvious to the skilled person. Such modifications and changes are intended to be embraced by the scope of the invention as defined by the appended claims.

We claim:

1. A method for measuring the flow rate differential through a dialysis machine including ultrafiltration means for effecting ultrafiltration and a heat exchanger including a primary side and a secondary side for exchanging heat between the flow of an inlet fluid having an inlet flow rate through said primary side of said heat exchanger into said dialysis machine and the flow of an outlet fluid have an outlet flow rate through said secondary side of said heat exchanger from said dialysis machine comprising measuring temperature differences across said primary and secondary sides of said heat exchanger and calculating said flow rate differential based upon said measured temperature differences and said one of said inlet flow rate or said outlet flow rate.

2. The method of claim 1 including determining the total flow rate of one of said inlet flow rate or said outlet flow rate, and wherein said calculating of said flow rate differential is based upon the equation $$\Delta Q = Q \times (\Delta T_1 - \Delta T_2)/\Delta T_2$$

wherein $\Delta Q$ comprises said flow differential, Q comprises said total flow rate of said one of said inlet flow rate or said outlet flow rate, $\Delta T_1$ comprises the temperature difference across one of said primary and secondary sides of said heat exchanger and $\Delta T_2$ comprises the temperature difference across the other of said primary and secondary sides of said heat exchanger.

3. The method of claim 2 wherein said determining of said total flow rate is carried out utilizing a nominal value of one of said inlet flow rate and said outlet flow rate.

4. The method of claim 3 wherein said nominal value is manually input.

5. The method of claim 2 wherein said dialysis machine includes a heater for heating one of said flow of said inlet fluid and said flow of said outlet fluid, and wherein said determining of said total flow rate includes measuring the temperature difference across said heater, and measuring the power supplied to said heater, wherein said determining of said total flow rate is based upon the equation $$Q = k \times P/\Delta T$$

wherein k comprises a constant, P comprises said power supplied to said heater, and $\Delta T$ comprises the temperature difference across said heater.

6. The method of claim 5 wherein said measuring of said power supplied to said heater is corrected for losses to the environment.

7. The method of claim 1 including determining heat capacities for said inlet fluid and said outlet fluid, and wherein said calculating of said flow rate differential includes compensating for differences in said heat capacities.

8. The method of claim 1 including determining heat energy losses in said heat exchanger and said dialysis machine, and wherein said calculating of said flow rate differential includes compensating for said heat energy losses.

9. Apparatus for measuring the flow rate differential through a dialysis machine comprising a flow inlet for a flow of an inlet fluid at an inlet flow rate to said dialysis machine, a flow outlet for a flow of an outlet fluid at an outlet flow rate from said dialysis machine, ultrafiltration means for effecting the flow of an ultrafiltration fluid in said dialysis machine, a heat exchanger including a primary side and a secondary side for exchanging heat between the flow of said inlet fluid in said flow inlet and the flow of said outlet fluid in said flow outlet, a temperature sensor for measuring temperature differences across said primary and secondary sides of said heat exchanger, and calculating means for calculating the said fluid flow rate differential based upon said measured temperature differences and said one of said inlet flow rate or said outlet flow rate.

10. The apparatus of claim 9 wherein said calculating means employs the equation $$\Delta Q = Q \times (\Delta T_1 - \Delta T_2)/\Delta T_2$$

wherein $\Delta Q$ comprises said flow rate differential, Q comprises the total flow rate of one of said flow of said inlet fluid or said flow of said outlet fluid, $\Delta T_1$ comprises the temperature difference across one of said primary and secondary sides of said heat exchanger, and $\Delta T_2$ comprises the temperature difference across the other of said primary and secondary sides of said heat exchanger.

11. The apparatus of claim 10 wherein said calculating means includes heat capacity compensation means for compensating for differences in the heat capacity of said inlet fluid and said outlet fluid, said heat capacity compensation means employing the equation $$\Delta Q_c/Q_1 = (1 - C_1/C_2) \times \Delta T_1/\Delta T_2$$

wherein $\Delta Q_c$ comprises a flow rate correction factor based upon said differences in said heat capacities, $Q_1$ comprises the total flow rate, $C_1$ comprises the heat capacity of said inlet fluid, and $C_2$ comprises the heat capacity of said outlet fluid.

12. The apparatus of claim 10 wherein said calculating means includes heat energy loss means for compensating for losses of heat energy in said heat exchanger and said dialysis machine, said heat energy loss means employing the equation $$\Delta Q_p/Q_1 = (131\ P_2/P_1) \times \Delta T_1/\Delta T_2$$

wherein $\Delta Q_p$ comprises a flow rate correction factor for said losses of heat energy, $Q_1$ comprises the total flow rate, $P_2$ comprises the heat energy loss in said flow of said inlet fluid and $P_1$ comprises the heat energy loss in said, flow of said outlet fluid.

13. The apparatus of claim 10 wherein said calculating means utilizes a nominal flow rate value for said total flow rate.

14. The apparatus of claim 13 wherein said nominal value is manually input.

15. The apparatus of claim 10 including a heater, temperature measuring means for measuring the temperature difference across said heater, and power measuring means for measuring the power supplied to said heater, wherein said calculating means is based upon the equation $$Q = k \times P / \Delta T$$

wherein k comprises a constant, P comprises said power supplied to said heater, and $\Delta T$ comprises the temperature difference across said heater.

16. The apparatus of claim 15 wherein said means for measuring said power supplied to said heater is corrected for the losses to the environment.

17. The apparatus of claim 9 including concentrate inlet means for the addition of a concentrate at a concentrate flow rate to said flow of said inlet fluid in said flow inlet.

18. The apparatus of claim 7 including a heater, wherein said heat exchanger and said heater include insulation jacket means.

19. A method for measuring a flow rate differential through a dialysis machine including:

a heat exchanger including a primary side and a secondary side for exchanging heat between an inlet fluid flow having an inlet flow rate through said primary side of said heat exchanger into said dialysis machine and an outlet fluid flow having an outlet flow rate through said secondary side of said heat exchanger from said dialysis machine; and ultrafiltration means for effecting an ultrafiltration fluid flow and thereby a flow rate addition to said outlet flow rate;

the method comprising the steps of measuring temperature differences across said primary and secondary sides of said heat exchanger;

determining the total flow rate of one of said inlet fluid flow and said outlet fluid flow; and calculating said flow rate differential by means of the equation:

$$\Delta Q = Q (\Delta T_1 - \Delta T_2) / \Delta T_2$$

wherein $\Delta Q$ is said flow rate differential,

Q is the total flow rate of one of said inlet fluid flow and said outlet fluid flow, $\Delta T_1$ is the temperature difference across the other of said primary and secondary sides of said heat exchanger; and $\Delta T_2$ is the temperature difference across one of said primary and secondary sides of said heat exchanger.

20. Apparatus for measuring a flow rate differential through a dialysis machine comprising:

a flow inlet for an inlet fluid flow to said dialysis machine, a flow outlet for an outlet fluid flow from said dialysis machine, a heat exchanger including a primary side and a secondary side for exchanging heat between said inlet fluid flow having an inlet flow rate through said primary side of said heat exchanger into said dialysis machine and said outlet fluid flow having an outlet flow rate through said secondary side of said heat exchanger from said dialysis machine;

ultrafiltration means for effecting an ultrafiltration fluid flow and thereby a flow rate addition to said outlet flow rate;

temperature sensor means for measuring temperature differences across said primary and secondary sides of said heat exchanger;

means for determining the total flow rate of one of said inlet fluid flow and said outlet fluid flow; and calculating means for calculating said flow rate differential by means of equation:

$$\Delta Q = Q \times (\Delta T_1 - \Delta T_2) / \Delta T_2$$

wherein $\Delta Q$ is said flow rate differential,

Q is the total flow rate of one of said inlet fluid flow and said outlet fluid flow, $\Delta T_1$ is the temperature difference across the other of said primary and secondary sides of said heat exchanger; and $\Delta T_2$ is the temperature difference across one of said primary and secondary sides of said heat exchanger.

* * * * *

UNITED STATES PATENT AND TRADEMARK OFFICE
CERTIFICATE OF CORRECTION

PATENT NO. : 5,714,685
DATED : February 3, 1998
INVENTOR(S) : Hobro et al.

It is certified that error appears in the above-indentified patent and that said Letters Patent is hereby corrected as shown below:

Column 2, line 19, delete "outlet flow".

Column 3, line 30, "if" should read --of--.

Column 6, line 34, delete "20".

Column 7, line 2, delete "20".

Column 7, line 6, delete "25".

Column 8, line 51, "$(-T_1 + T_4) = -T_2$"
should read --$(-T_1 + T_4) = -\Delta T_2$--.

Column 12, line 59, "$\Delta Q_p/Q_1 = (131\ P_2/P_1) \times \Delta T_1/\Delta T_2$"
should read --$\Delta Q_p/Q_1 = (1 - P_2/P_1) \times \Delta T_1/\Delta T_2$--

Column 12, line 63, "said, flow" should read --said flow--.

Column 13, line 20, "7" should read --9--.

UNITED STATES PATENT AND TRADEMARK OFFICE
CERTIFICATE OF CORRECTION

PATENT NO. : 5,714,685
DATED : February 3, 1998
INVENTOR(S) : Hobro et al.

It is certified that error appears in the above-indentified patent and that said Letters Patent is hereby corrected as shown below:

Column 13, line 43, "$\Delta Q = Q(\Delta T_1 - \Delta T_2)/\Delta T_2$" should read --$\Delta Q = Q \times (\Delta T_1 - \Delta T_2)/\Delta T_2$--.

Signed and Sealed this

Eleventh Day of August 1998

Attest:

BRUCE LEHMAN

*Attesting Officer*  *Commissioner of Patents and Trademarks*